US009629394B2

(12) United States Patent
Aronie et al.

(10) Patent No.: US 9,629,394 B2
(45) Date of Patent: Apr. 25, 2017

(54) PORTABLE VAPORIZER WITH CENTRAL PIN HEATER HAVING HEAT DIFFUSER-MIXER BLADES

(71) Applicants: Alan Benet Aronie, Littleton, MA (US); Joel Aronie, Chilmark, MA (US)

(72) Inventors: Alan Benet Aronie, Littleton, MA (US); Joel Aronie, Chilmark, MA (US)

(*) Notice: Subject to any disclaimer, the term of this patent is extended or adjusted under 35 U.S.C. 154(b) by 777 days.

(21) Appl. No.: 14/086,673

(22) Filed: Nov. 21, 2013

(65) Prior Publication Data

US 2015/0136124 A1    May 21, 2015

(51) Int. Cl.
| | | |
|---|---|---|
| *A24F 47/00* | (2006.01) | |
| *A61M 15/00* | (2006.01) | |
| *A61M 15/06* | (2006.01) | |
| *A61M 16/10* | (2006.01) | |
| *A61M 11/04* | (2006.01) | |

(52) U.S. Cl.
CPC ......... *A24F 47/008* (2013.01); *A61M 11/042* (2014.02); *A61M 15/0021* (2014.02); *A61M 15/0086* (2013.01); *A61M 15/06* (2013.01); *A61M 2205/3653* (2013.01); *A61M 2205/8206* (2013.01); *A61M 2205/8237* (2013.01)

(58) Field of Classification Search
CPC . A24F 47/008; A61M 15/06; A61M 15/0021; A61M 15/0086; A61M 16/109
USPC .................................................... 128/202.21
See application file for complete search history.

(56) References Cited

U.S. PATENT DOCUMENTS

| | | | |
|---|---|---|---|
| 5,498,855 A * | 3/1996 | Deevi | A24F 47/008 |
| | | | 131/194 |
| 6,826,355 B2 | 11/2004 | Aronie et al. | |
| 8,488,952 B2 | 7/2013 | Landry | |
| 8,869,792 B1 * | 10/2014 | Lee | A61M 15/06 |
| | | | 128/202.21 |
| 2008/0023003 A1 * | 1/2008 | Rosenthal | A61M 11/041 |
| | | | 128/203.26 |
| 2008/0149118 A1 | 6/2008 | Oglesby et al. | |
| 2009/0095311 A1 * | 4/2009 | Han | A24F 47/008 |
| | | | 131/194 |
| 2012/0255546 A1 * | 10/2012 | Goetz | A61M 11/041 |
| | | | 128/202.21 |
| 2013/0037041 A1 | 2/2013 | Worm et al. | |

* cited by examiner

*Primary Examiner* — Joseph S Del Sole
*Assistant Examiner* — Mohamed K Ahmed Ali
(74) *Attorney, Agent, or Firm* — Jerome E Sacks, Patent Agent

(57) ABSTRACT

A device used for generating a breathable vapor from an herbal substance such as tobacco or medical marijuana. The device features a heater assembly having of a rod shape heating element with the heat diffuser-mixer blades attached, and is mounted in a case component having the shape of a tubular cylinder. The heater assembly and case component are configured so that the rod is centered within the tubular cylinder. An herbal chamber, which accommodates an herbal substance, is rotationally and removably insertable into the case component tubular cylinder. A mouthpiece is attachable to the herbal chamber, with a screen component. When electrical power is applied to the heater assembly, the herbal substance is vaporized. The device may also be configured to function as an e-cigarette or an essential oil vaporizer. Rotating the herbal chamber causes the herbal substance to be redistributed.

11 Claims, 8 Drawing Sheets

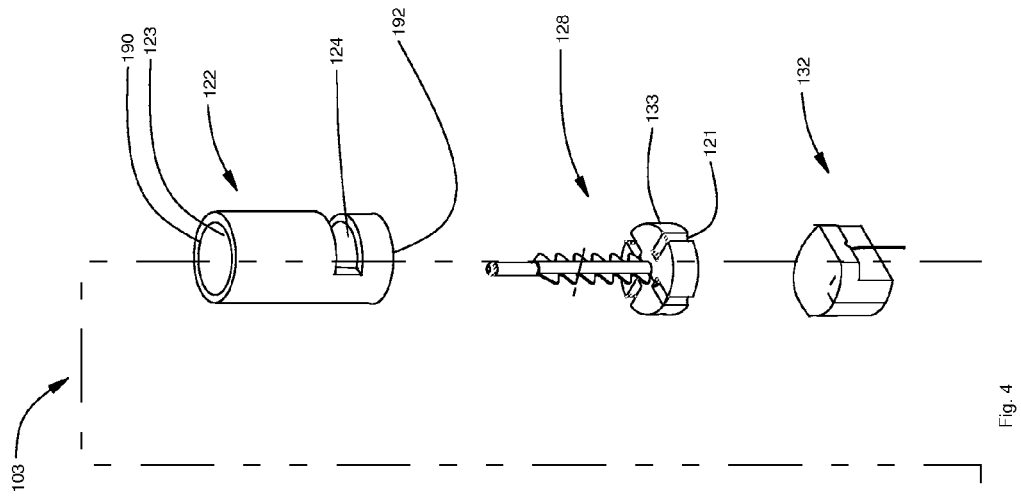
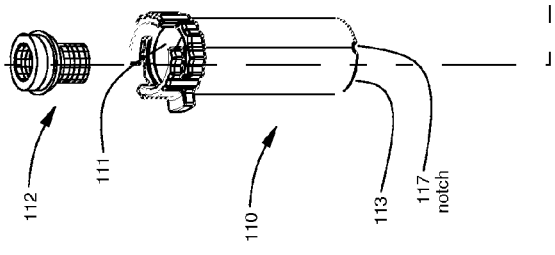
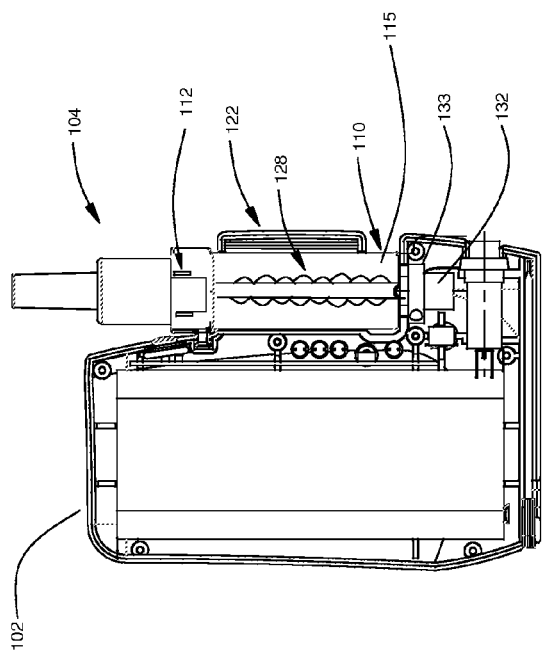
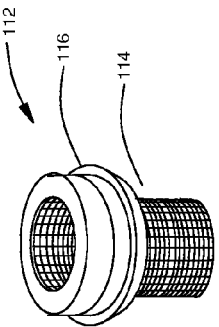

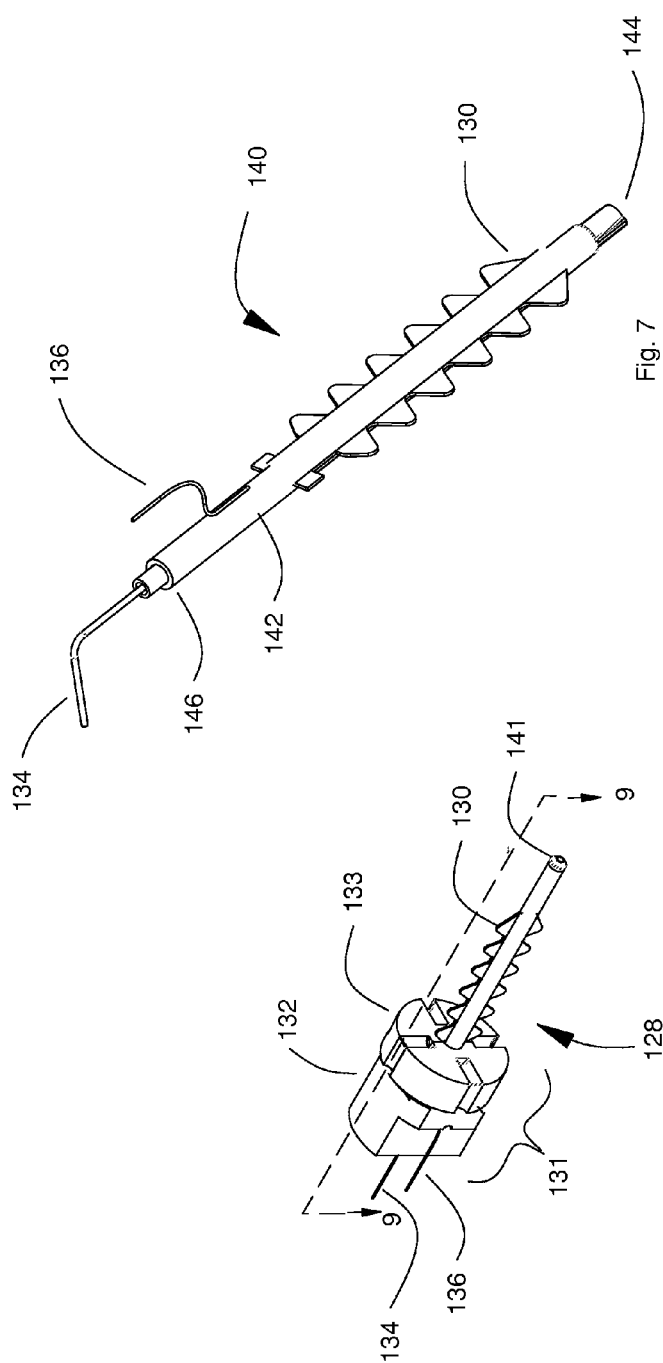

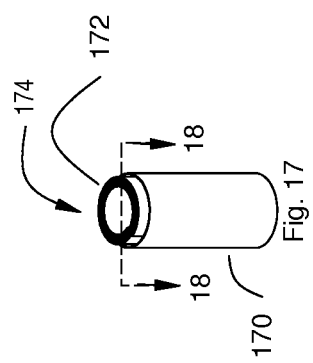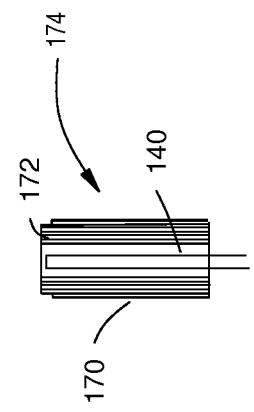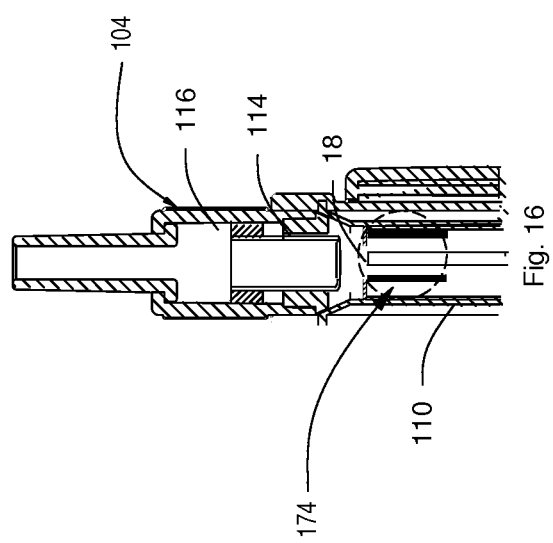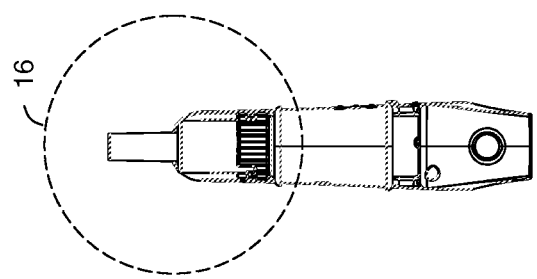

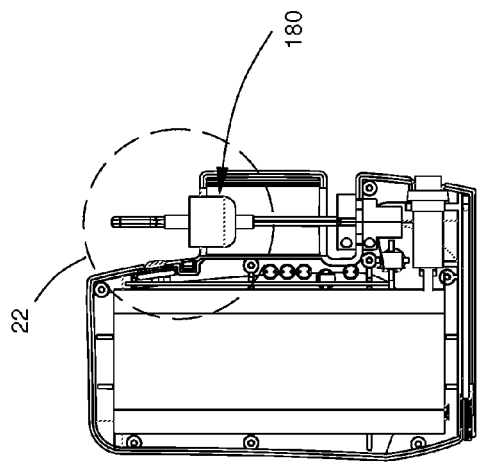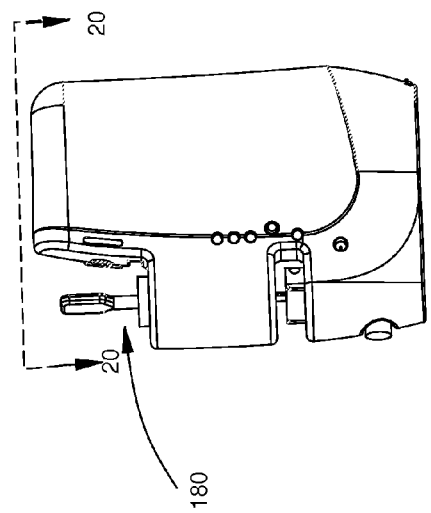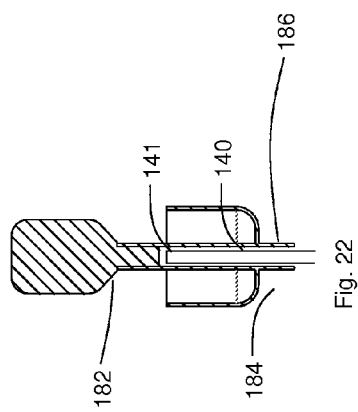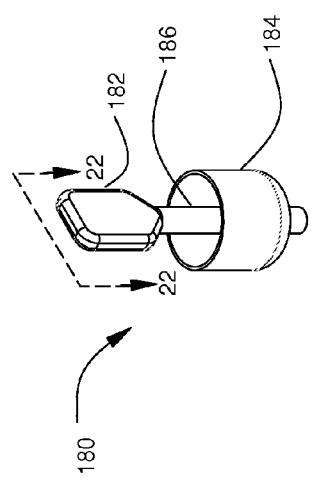

PORTABLE VAPORIZER WITH CENTRAL PIN HEATER HAVING HEAT DIFFUSER-MIXER BLADES

CROSS-REFERENCE TO RELATED APPLICATIONS

This application claims the benefit of the U.S. Provisional Patent Application No. 61/853,619 filed on Apr. 9, 2013 by the present inventors. This provisional patent application is incorporated herein by reference

BACKGROUND OF THE INVENTION

Many vaporizers have been proposed that use electrical power or solid or liquid fuel to vaporize herbal substances such as tobacco or medical marijuana. These vaporizers have the advantage of vaporizing the herbal substance without combustion, thereby avoiding the combustion that has negative health and environmental results, as well as creating a fire hazard. Typically, these vaporizers have an herbal chamber where the herbal material is placed and heating elements that either surround the herbal chamber on the outside, or have coils that spiral within the herbal chamber. The herbal chamber has an herbal chamber cavity that extends the length of the herbal chamber. Other heating mechanisms are also used, where heated air may be forced through the chamber. In addition, many have a flat screen on its mouthpiece end that prevents the herbal substance from being entering the mouthpiece.

SUMMARY OF THE INVENTION

The first embodiment of the vaporizer presented herein generates a breathable vapor from an herbal substance such as tobacco or medical marijuana. The vaporizer features a heater assembly having a pin heater component with a pin heater in the shape of a thin rod with attached pin heater base and heat diffuser-mixer blades. The pin heater component is mounted in a case component having the shape of a tubular cylinder. The heater assembly and case component are configured so that the pin heater is centered within the tubular cylinder. An herbal chamber, part of the heater assembly, accommodates an herbal substance. The herbal chamber is rotationally and removably insertable into the case component tubular cylinder. A mouthpiece is removably attachable to the herbal chamber, with a screen component having a screen with a shape of a thimble. When electrical power is applied to the heater component, the pin heater is heated, the heat diffuser-mixer blades distribute the heat to the surrounding air and herbal substance, and vaporization occurs.

Among the novel features of the various embodiments are:
- when the herbal chamber is rotated while installed in the case component, the diffuser-mixer blades mix the herbal substance;
- the herbal chamber may be filled from either its top (removing only the mouthpiece), or the bottom (after removing it from the case component);
- the screen is shaped like a thimble instead of a flat surface; thereby reducing the likely hood of clogging, and makes drawing of the vapor from the herbal chamber easier;
- the location of the rod of the heater pin with heat diffuser-mixer blades positioned along the longitudinal center of the herbal chamber radially distributes the heat within the herbal chamber efficiently, thereby saving the battery charge.

The device may also be configured to function as an E-cigarette or an essential oil vaporizer.

LIST OF FIGURES

FIG. 3 is a cutout view of the first embodiment of the present invention.

FIG. 4 is an exploded perspective view of the main components of the first embodiment of the present invention.

FIG. 5 is a perspective view of the screen component of the first embodiment of the present invention.

FIG. 6 is a perspective view of the heater component and heater base of the first embodiment of the present invention.

FIG. 7 is a perspective view of the pin heater with attached diffusion blades of the first embodiment of the present invention.

FIG. 8 is a perspective view of the heating coil with two attached leads of the first embodiment of the present invention.

FIG. 15 illustrates a side view of the first embodiment of the present invention.

FIG. 16 illustrates a sectional view of a detail of FIG. 15 in an expanded scale.

FIG. 17 illustrates a perspective view of the capillary component in the E-cigarette mode of the first embodiment of the present invention.

FIG. 18 illustrates a sectional view of FIG. 17.

FIG. 19 is a perspective view of the first embodiment of the present invention configured in the essential oil mode.

FIG. 20 is a section view of the first embodiment of the present invention when in the essential oil mode.

FIG. 21 is a perspective view of the aroma cup component of the first embodiment of the present invention.

FIG. 22 is a sectional view of a detail of FIG. 20.

DETAILED DESCRIPTION OF THE DISCLOSURE

As used in this detailed specification, the terms left, right, top and bottom refer to the figure under discussion. If more than one identical part is shown on a figure, only one numeral lead line may be indicated on the figure. In the following detailed description the various embodiments will be referred to as the vaporizer. The term heat diffuser-mixer blades is understood generally to refer to one or more appendages located on the pin heater rod on the pin heater that will aid in mixing an herbal substance and aid in heat dissipation.

Figure 1:
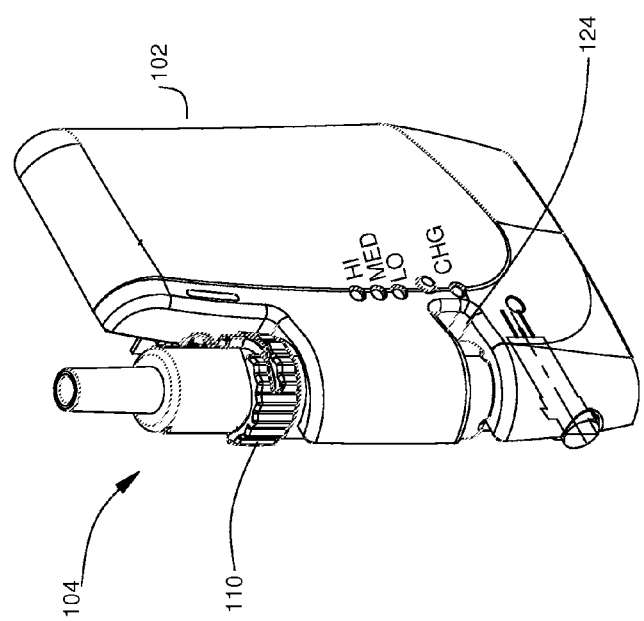
FIG. 1 is a perspective view of the first embodiment of the present invention.
Figure 2:
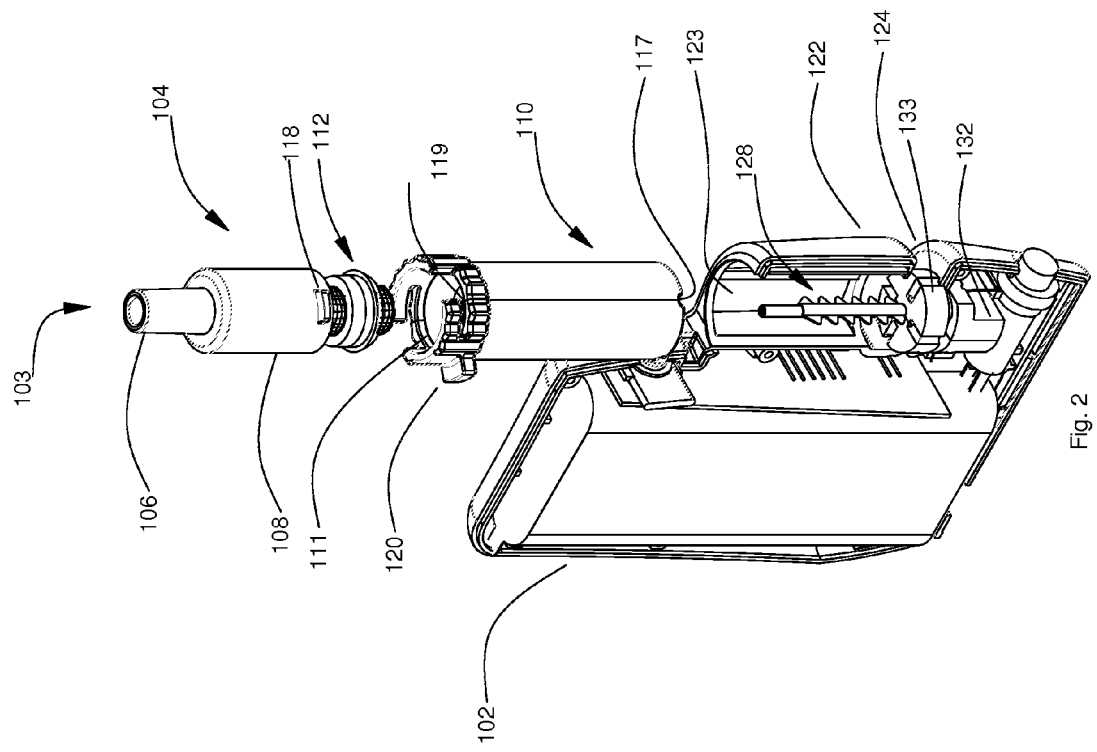
FIG. 2 is a perspective, partially cutout, partially exploded view of the first embodiment of the present invention.

FIG. 1 illustrates a front perspective view of a first embodiment of the present invention configured to be used with an herbal substance such as tobacco or medical marijuana. This vaporizer use is referred to as the herbal mode. FIG. 2 illustrates a rear cutout, partially exploded view of the first embodiment of the present invention. FIG. 3 illustrates a cutout view of the heater assembly installed in case 102. FIG. 4 is an exploded perspective view of the heater assembly 103. FIG. 5 illustrates, in expanded scale, the screen component 112.

Referring to FIGS. 1 through 8, the following terms are used:

The heater assembly 103 consists of the mouthpiece component 104, the screen component 112, the herbal chamber 110, the case chamber 122, (which is part of the case 102), and pin heater component 128 as illustrated in FIG. 4.

The pin heater component 128 consists of the case heater base 132, the pin heater base 133 and the pin heater 140 as illustrated in FIGS. 6 and 8. The case heater base 132 and the pin heater base 133, when combined in a single component are referred to as the combined heater base 131.

The pin heater 140 consists of the external tube 142, glass tube 146, heating coil 148, plug 144, heating coil top lead 136, heating coil bottom lead 134, lead connector 138, and heat diffuser-mixer blades 130, as illustrated in FIGS. 6 and 7. The pin heater without the heat diffuser-mixer blades attached denotes a rod component 135 having the shape of a rod.

Referring to FIGS. 1 through 5, a mouthpiece component 104 is comprised of a mouthpiece 106, and an extension 108; mouthpiece 106 is slidingly attached to extension 108. Screen component 112 is comprised of screen holder 116 and attached screen 114. The attached screen 114 has the shape of a thimble. Screen component 112 fits into the bottom of mouthpiece component 104. Mouthpiece component 104 is removably attached to herbal chamber 110. The herbal chamber 110 having an herbal chamber cavity 115 in the shape of a tubular cylinder. The mouthpiece component 104 is removably securable to herbal chamber 110 by fitting its bottom end into the herbal chamber vapor exhaust end 111 of herbal chamber 110, and then twisting it a quarter turn, thereby securing the herbal chamber 110 to mouthpiece component 104. The securing is achieved by first lock tab 118 located on the bottom side of mouthpiece component 104, which removably locks the extension locking slot 119 located on the top of herbal chamber 110. The mouthpiece component, screen component, and herbal chamber component are configured so that screen component 112 is held firmly in place in the mouthpiece component 104, and fits snugly in the herbal chamber vapor exhaust end 111 of the herbal chamber 110 when assembled.

Case 102 has a case chamber 122 that hosts the herbal chamber 110. Referring to FIGS. 4 and 6, case chamber 122 has a case chamber cavity 123 extending along the length of the case chamber cavity 123 along its longitudinal direction, the case tubular cavity has a circular cross section, a case chamber exhaust end 190 and a case chamber air intake end 192. The herbal chamber 110 has an herbal chamber cavity 115 extending the length of the herbal chamber 110; the herbal chamber cavity 115 having a circular cross section. The case heater base 132 is attached to case 102. Pin heater 140 is attached to the case heater base 132.

FIG. 3 illustrates the components of the heater assembly when installed in the case 102. FIG. 4 illustrates an exploded perspective view of heater assembly 103. Referring to FIGS. 3 and 4, mouthpiece component 104 is installed on herbal chamber 110 with screen component 112 removably attached to mouthpiece component 104. Case heater base 132 of pin heater component 128 is attached to case 102. Herbal chamber 110 is rotationally mounted within case chamber 122 and is removably secured using second lock tab 120. When the heater assembly 103 (see FIG. 4) is assembled as illustrated in FIG. 3, the rod component 135 of the pin heater component is positioned along the longitudinal center of the herbal chamber.

Figure 9:
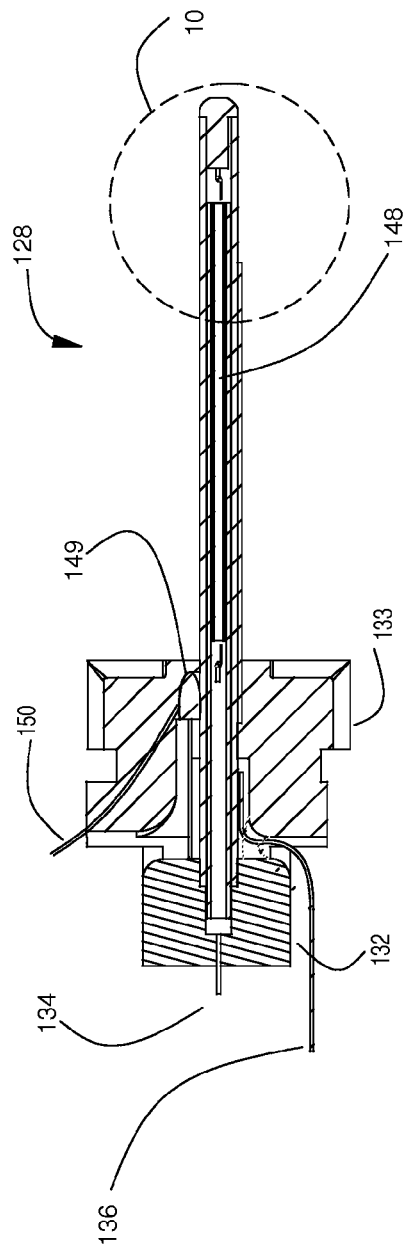
FIG. 9 is a sectional view of FIG. 6.
Figure 10:
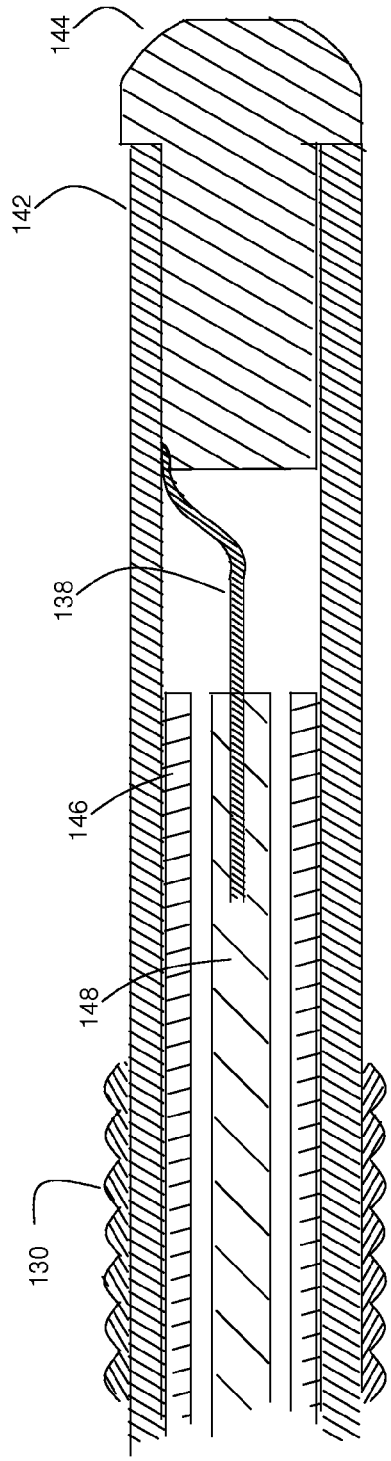
FIG. 10 is a sectional view of a detail of FIG. 9.

FIG. 6 illustrates the pin heater component 128 consisting of the case heater base 132 and the pin heater 140 having a pin heater base 133, and a rod component 135 having the shape of a rod with heat diffuser-mixer blades 130 attached. The case heater base 132 and the pin heater base 133 together are referred to as the combined heater base 131. Pin heater 140 has a pin heater end 141 locate on the opposite end from the case heater base 132. The FIG. 7 is a perspective view of pin heater 140. FIG. 8 illustrates the heating coil 148 imbedded in the pin heater 140 with heating coil bottom lead 134 and lead connector 138. FIG. 9 illustrates a sectional view of pin heater component 128 (heat diffusion blades not shown). FIG. 10 illustrates a detail of FIG. 9.

Referring to FIGS. 9 and 10, the pin heater component 128 has the heating coil 148 encased in a glass tube 146, which itself is encased in external tube 142. External tube 142 is capped on its right side by a plug 144. The lead connector 138 is attached to external tube 142 by crimping it between external tube 142 and plug 144. The heating coil top lead 136, heating coil bottom lead 134, and lead connector 138 are all made of copper, the heating coil 148 is made of resistance wire used for heating, and the external tube 142 is made of stainless steel. The glass tube 146, made of heat resistant glass, act as an insulator, so there is an electrically conductive path from the heating coil bottom lead to the heating coil top lead. When external power is applied across these leads, the heating coil will heat the external tube and the heat diffuser-mixer blades 130, which then radially heats the air and herbal substance in the herbal chamber. The temperature in the herbal chamber will depend on the amount of electrical power applied. Referring to FIG. 9, a thermistor 149, located on the pin heater base 133, relays the temperature of the pin heater to the PCB lead 150, which then adjusts the power level so that the requested temperature is maintained.

Referring to FIGS. 1, 2, 4, 6, 8 and 9, there are four notches 117 on the bottom of herbal chamber 110, and four air intake slots 121 on the case heater base 132. The four notches 117 and four air intake slots 121 are configured so that a proper amount of air enters the herbal chamber 110 when the vaporizer is being used. The side air opening 124 of the case 102 permits the air to enter the herbal chamber 110. Proper amount of air means the amount of air required for effective drawing of air for using the vaporizer.

Figure 12:
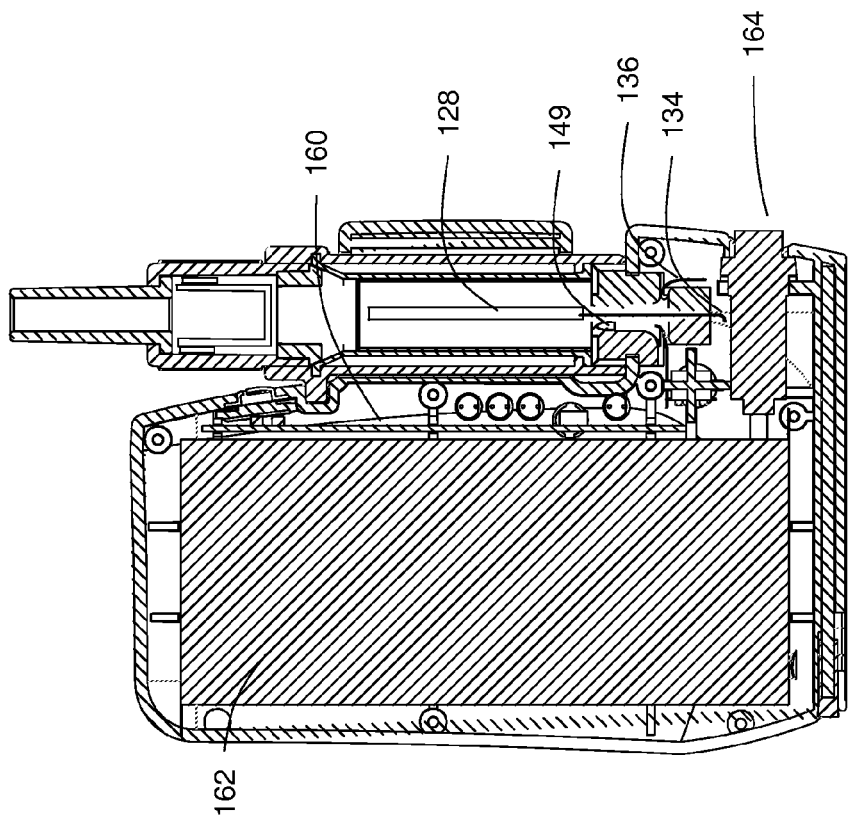
FIG. 12 is a sectional view illustrating some of the parts of the electrical system of the first embodiment of the present invention.
Figure 11:
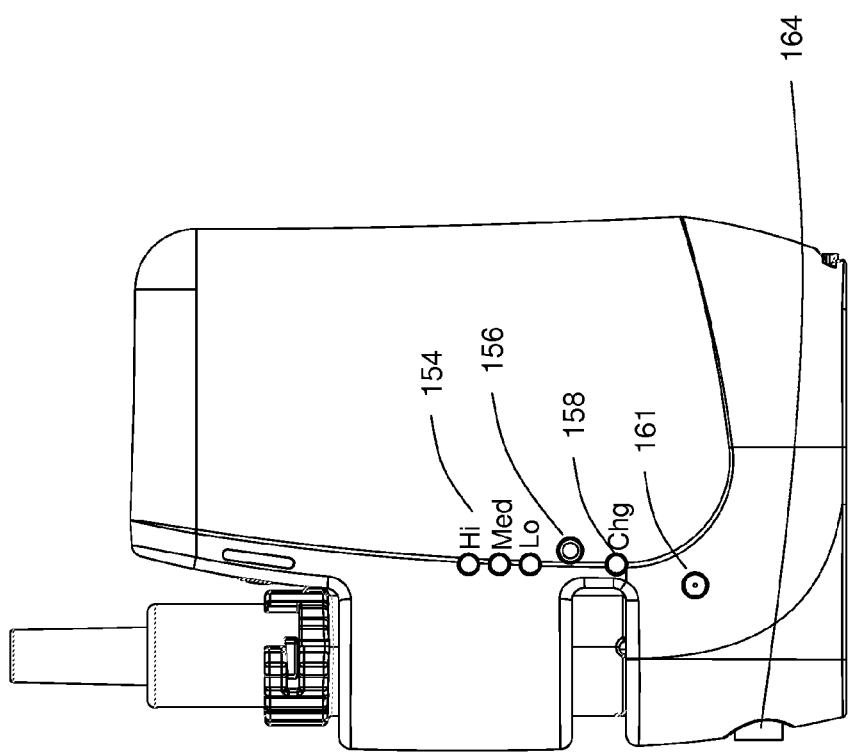
FIG. 11 is a side view illustrating some of the electrical parts of the first embodiment of the present invention.

FIG. 11 illustrates a front view of the portable vaporizer, illustrating the electrical parts, and FIG. 12 illustrates a sectional view of the portable vaporizer illustrating electrical parts. Referring to FIGS. 11 and 12, the PCB board 160 provides the logic circuits that control the other electrical parts. All the other electrical parts connect to the PCB board. The battery 162 provides electrical power to the electrical system. In the first embodiment it is a rechargeable battery pack. The on/off switch 164 turns the portable vaporizer on or off. The heat selection switch 156 allows the user to select the desired heat level (Hi, Medium, and Low), which is indicated to the user by which of the three temperature indicator lights 154 is lit. The recharge indicator light 158 indicates when the battery needs charging, and the charging port 161 is used to charge the portable vaporizer. (The charger, which runs off 120 volts in USA or 240 volts in Europe, is not shown in the figures). The heating coil top lead 136 and the heating coil bottom lead 134 receive the proper electrical power from the battery 162 to heat the pin heater 140 to the desired temperature (Hi, Medium, Low) as selected by the heat selection switch 156. The thermistor 149 senses the temperature in the case heater base 132 and provides this data to the PCB board 160 to adjust the pin heater 140 temperature.

Figure 14:
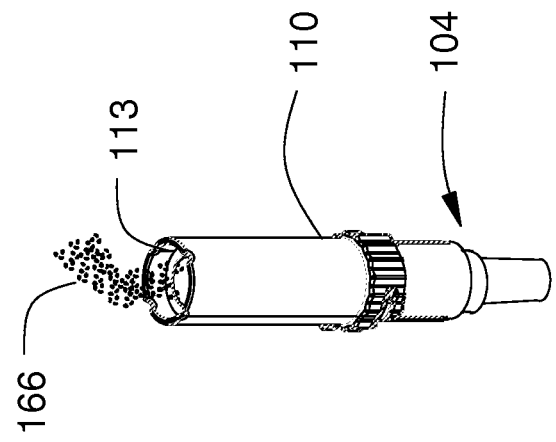
FIGS. 13 and 14 illustrate two methods of filling the herbal chamber of the first embodiment of the present invention.
Figure 13:
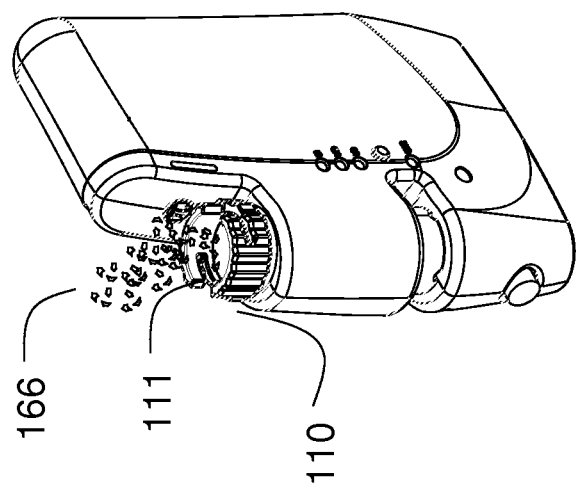

FIGS. 13 and 14 illustrate two methods on how the portable vaporizer is loaded with an herbal substance 166. With the first method, the mouthpiece component with the screen component 112 attached, is removed while the herbal chamber 110 is securely mounted in the case chamber 122 of the case 102. Holding the portable vaporizer upright, the herbal substance 166 is poured into the herbal chamber vapor exhaust end 111. For the second loading method, the herbal chamber 110, with the mouthpiece component and screen component 112 attached, is removed from the portable vaporizer and turned upside down, as illustrated in FIG. 14. The herbal substance 166 is inserted into the herbal chamber air intake end 113 of the herbal chamber 110. Then, holding the case 102 upside down, the herbal chamber 110 with the mouthpiece component attached is inserted in the case chamber 122 and secured.

Among the many desirable features of the vaporizer is the attached screen 114 constructed out of small gauge stainless steel in the shape of a thimble that makes the drawing of the exhaust vapor easier, is less likely to clog, and is easier to clean. The pin heater component 128 heats the air and tobacco or herbal material radially from the center of the herbal chamber towards the outside wall of the holder. The pin heater component 128 has heat diffuser-mixer blades 130 made of stainless steel welded on for improving the heat distribution throughout the herbal chamber. The heat diffuser-mixer blades 130 also act to mix the substance in the herbal chamber 110 when the herbal chamber is rotated back and forth. The central location of the pin heater with the heat diffusion blades efficiently heats the herbal substance, thereby conserving battery charge. Furthermore, as shown in the discussion of FIGS. 13 and 14, the herbal chamber 110 can be loaded with material in two ways: a) from the top, while installed in the vaporizer or b) when the holder is removed from the vaporizer body, which makes loading easier than when the tube holder is installed. Also, cleaning is easily accomplished with the herbal chamber removed from the case and the screen component removed from the herbal chamber.

FIGS. 15 through 18 present various views of the portable vaporizer used in an E-cigarette mode. FIG. 15 illustrates a front view of the portable vaporizer, and FIG. 16 indicates a sectional view of the relevant details of the parts in this mode. Referring to FIG. 16, the portable vaporizer in the cigarette mode has added a capillary component 174. FIG. 17 illustrates a perspective view of the capillary component 174. It consists of a rolled screen 172 made of stainless steel encased in a stainless steel tube herein called an e-tube 170. FIG. 18 gives a sectional view of capillary component 174; the sectional view indicates how it is positioned relative the pin heater 140.

To use the portable vaporizer in the E-cigarette mode, the mouthpiece component 104 with the screen holder 116 with attached screen 114 is removed for the portable vaporizer, and the capillary component 174 is installed in the herbal chamber 110, striding the pin heater 140 as indicated in FIG. 14. The E-cigarette vapor product, typically a liquid, is added to the capillary component 174, and the mouthpiece component 104 with the screen holder 116 with attached screen 114 is reattached to the herbal chamber 110. The vaporizer is then ready to be used in the E-cigarette mode. The E-cigarette mode is effective since the capillary component 174 uses capillary action to ensure the liquid vapor product is distributed on the rolled screen 172 in an approximately uniform manner.

FIGS. 19 through 22 present various views of the portable vaporizer used in an essential oil vaporizer mode. FIG. 19 illustrates a side perspective view of the vaporizer in an essential oil vaporizer mode. In this mode, an aroma cup component 180 replaces the mouthpiece component 104 of the herbal mode. FIG. 20 illustrates a sectional view of the vaporizer with the aroma cup component 180 installed. FIG. 21 illustrates a perspective view of the aroma cup component 180. It has an aroma cup 184 with a handle 182 that is attached to a handle shaft 186 that goes through the longitudinal center of the aroma cup as indicated in FIG. 21. FIG. 22 is a sectional view of the aroma cup component 180 installed on the pin heater component 128. The aroma cup component 180 in the first embodiment is made out of material that can handle the high heat generated by the pin heater component 128.

To use the vaporizer in the essential oil vaporizer mode, the aroma cup component 180 is installed as indicated in the previous paragraph; the vaporizer is positioned so that the aroma cup can hold an essential oil and the essential oil of choice is added to the aroma cup. When vaporizer is turned on, the essential oil will vaporize.

Additional embodiments are consistent with the inventive concepts presented herein. The case may be made smaller, using smaller batteries; either rechargeable or non-rechargeable batteries. Only one or two of the three modes may be implemented. The materials used, e.g. stainless steel, copper, and glass may be replaced by different materials with appropriate properties of insulation and electrical conductivity. The notches may be any air opening on the herbal chamber that permits a controlled amount of air into the herbal chamber. The case heater base and the pin heater base may be combined as a single component, called the combined heater base.

The disclosure presented herein gives several embodiments of the invention. These embodiments are to be considered as only illustrative of the invention and not a limitation of the scope of the invention. Various permutations, combinations, variations and extension of these embodiments are considered to fall within the scope of this invention. Therefore the scope of this invention should be determined with reference to the claims and not just by the embodiments presented herein.

What is claimed is:

1. A vaporizer capable of vaporizing an herbal substance, said vaporizer comprised of:
    an herbal chamber, said herbal chamber comprised of an herbal chamber cavity having a shape of a tubular cylinder, said herbal chamber cavity having a longitudinal center, said herbal chamber having a herbal chamber vapor exhaust end and a herbal chamber air intake end;
    a mouthpiece component, said mouthpiece component removably attachable to said herbal chamber at said herbal chamber vapor exhaust end;
    a pin heater component, said pin heater component comprised of a pin heater in a shape of a rod, and a combined heater base attached to said pin heater;

said pin heater component being sized and configured such that said herbal chamber is capable of being inserted over said pin heater component such that said herbal chamber air intake end being mountable on said combined heater base with said rod being centered along said longitudinal center of said herbal chamber, said herbal chamber air intake end have an air opening that allows air to enter, said pin heater component having electric power connections such that when electrical power is applied to said pin heater component, then said rod of said pin heater radially heats said herbal chamber, said vaporizer further comprising a screen component, said screen component comprised of a screen in a shape of a thimble, said screen component removably attachable to said vaporizer securely positioned between said screen component and said herbal chamber vapor exhaust end;

said vaporizer further comprised of at least one heat diffuser-mixer blade attached to said pin heater such that when said pin heater is heated, then said at least one heat diffuser-mixer blade radiates heat inside of said herbal chamber thereby vaporizing said herbal substance inserted in said herbal chamber.

2. The vaporizer of claim 1 further comprised of a case component, said case component having a case chamber cavity, and a side air opening, said case component attached to said pin heater component at said combined heater base, said herbal chamber rotationally and securably mountable in said case chamber cavity wherein when said herbal chamber is rotationally and snugly mounted on said case chamber cavity, and said herbal substance added to said herbal chamber cavity, and said mouthpiece component attached to said herbal chamber at said herbal chamber vapor exhaust end, then rotating said herbal chamber is capable of mixing said herbal substance.

3. A vaporizer capable of vaporizing an herbal substance, said vaporizer comprised of:
a case chamber, said case chamber having a case chamber cavity having the shape of a tubular cylinder extending the length of said case chamber;
an herbal chamber, said herbal chamber having the shape substantially of a tubular cylinder, said herbal chamber having a herbal chamber cavity, said herbal chamber cavity having a herbal chamber vapor exhaust end and a herbal chamber air intake end, said herbal chamber sized and configured so that it rotationally, removably, and snugly fits inside said case chamber cavity;
a pin heater component; said pin heater component comprising:
a pin heater, said pin heater having the shape of a rod having a longitudinal axis, said pin heater mounted on a combined heater base, said combined heater base attached to said case chamber;
said pin heater component sized and configured such that when said combined heater base is attached said case chamber, then said longitudinal axis of said pin heater coincides with the longitudinal axis of said case chamber;
said pin heater having electrical circuitry capable of heating to a range of temperatures when electrical power is applied to said pin heater thereby radiates heat to said herbal chamber cavity;
a mouthpiece component, said mouthpiece component being removably attachable to said herbal chamber such that when said mouthpiece component is rotated, said herbal chamber is rotated around said pin heater;

wherein when said herbal substance is added to said herbal chamber, said mouthpiece component is attached to said herbal chamber vapor exhaust end, and said pin heater component is heated, a vapor is generated emanating from said herbal chamber vapor exhaust end.

4. The vaporizer of claim 3 wherein said pin heater component additionally comprises at least one heat diffuser-mixer blade attached to said pin heater, such that when said pin heater is heated, then said at least one heat diffuser-mixer blade radiates heat to said herbal chamber cavity.

5. The vaporizer of claim 3 additionally comprised of a screen component, said screen component removably securable between said mouthpiece component and said herbal chamber, said screen component having a screen shaped like a thimble, said screen having a gauge so it allows said vapor to pass through but prevents said herbal substance placed in said herbal chamber passing through.

6. The vaporizer of claim 3 additionally having a capillary component comprised of a rolled tube of mesh material enclosed in an e-tube made of stainless steel such that if said capillary component is installed in said pin heater component so it is positioned inside of said herbal chamber cavity around said pin heater, such that when an E-cigarette vapor product is added to said capillary component, said heating said pin heater will cause said E-cigarette vapor product to vaporize.

7. The vaporizer of claim 3 additionally having an aroma cup component, said aroma cup component comprised of an aroma cup installable on a pin heater end such that when said aroma cup is installed on said pin heater end replacing said mouthpiece component, and an essential oil is added to said aroma cup, said essential oil is vaporized when said pin heater is heated.

8. A vaporizer for vaporizing an herbal substance, said vaporizer comprised of:
a case hosting a case chamber, said case chamber having a case chamber exhaust end, a case chamber air intake end, and a side air opening;
a heater assembly, said heater assembly comprised of:
an herbal chamber, said herbal chamber having a herbal chamber cavity extending the length of said herbal chamber, said herbal chamber having a herbal chamber air intake end and a herbal chamber vapor exhaust end, said herbal chamber sized and configured so that it rotationally, removably, and snugly fits inside said case chamber;
a pin heater component; said pin heater component comprising:
a case heater base, said case heater base attached to said case chamber at said case chamber air intake end, said case heater base additionally having at least one air intake slot allowing air to enter, said at least one air intake slot positioned at said side air opening;
a pin heater, said pin heater attached to said case heater base, said pin heater having a shape of a rod with at least one heat diffuser-mixer blade attached to said pin heater, said pin heater having a longitudinal axis, said longitudinal axis coincides with the longitudinal axis of said herbal chamber cavity;
said pin heater capable of heating to a range of temperatures when electrical power is applied to said pin heater;
said pin heater component sized and configured such that when said pin heater component is attached said case chamber, then said longitudinal axis of said pin heater coincides with the longitudinal axis of said case chamber;

a mouthpiece component, said mouthpiece component removably attachable to said herbal chamber vapor exhaust end such that if said mouthpiece component is attached to said herbal chamber vapor exhaust end, and said herbal chamber vapor exhaust end is rotated, then said herbal chamber is rotated around said pin heater;

a screen component, said screen component removably securable between said mouthpiece component and said herbal chamber, said screen component having a screen shaped like a thimble, said screen having a gauge so it allows a vapor to pass through but prevents said herbal substance placed in said herbal chamber passing through;

wherein when said herbal substance is added to said herbal chamber, said mouthpiece component is attached to said herbal chamber vapor exhaust end, and said pin heater component is heated, said vapor is generated emanating from said herbal chamber vapor exhaust end.

9. The vaporizer of claim 8 wherein said pin heater is comprised of:

a heating coil; said heating coil constructed out of an electrically conductive material;

an insulated tube, said insulated tube containing said heating coil;

an external tube; said external tube containing said insulated tube;

said heating coil electrically connected to a heating coil top lead at a first heating coil end; a heating coil second end electrically connected to said external tube such than when said electrical power is applied to said heating coil top lead and to said external tube, then said pin heater is heated.

10. The vaporizer of claim 9 wherein said heating coil is made of resistance wire, said insulated tube is made of glass, and said external tube is made of stainless steel.

11. The vaporizer of claim 8 wherein said electrical power is provided by a portable battery.

\* \* \* \* \*